United States Patent
Ward

(10) Patent No.: US 7,891,531 B1
(45) Date of Patent: Feb. 22, 2011

(54) SUB-MINIATURE SURGICAL STAPLE CARTRIDGE

(76) Inventor: Gary L. Ward, 395 N. Range Line Rd., Pleasant Hill, OH (US) 45359

( * ) Notice: Subject to any disclaimer, the term of this patent is extended or adjusted under 35 U.S.C. 154(b) by 0 days.

(21) Appl. No.: 11/699,170

(22) Filed: Jan. 29, 2007

Related U.S. Application Data

(60) Provisional application No. 60/763,571, filed on Jan. 31, 2006.

(51) Int. Cl.
*A61B 17/072* (2006.01)
(52) U.S. Cl. .................... 227/175.1; 227/176; 227/178; 227/19; 227/156; 606/219
(58) Field of Classification Search .................. 227/176, 227/178, 19, 156, 175.1; 606/219
See application file for complete search history.

(56) References Cited

U.S. PATENT DOCUMENTS

| | | | | |
|---|---|---|---|---|
| 3,068,564 A | * | 12/1962 | Wiedt, Jr. .................... 228/175 |
| 4,589,582 A | * | 5/1986 | Bilotti .......................... 227/19 |
| 4,805,823 A | * | 2/1989 | Rothfuss ...................... 227/19 |
| 4,978,049 A | * | 12/1990 | Green ...................... 227/178.1 |
| 5,470,008 A | * | 11/1995 | Rodak ...................... 227/176.1 |
| 5,630,541 A | * | 5/1997 | Williamson et al. ....... 227/178.1 |
| 5,653,928 A | * | 8/1997 | Schnipke ..................... 264/138 |
| 5,871,135 A | | 2/1999 | Williamson, IV et al. |
| 5,919,198 A | | 7/1999 | Graves, Jr. et al. |
| 6,066,144 A | * | 5/2000 | Wolf et al. ................... 606/139 |
| 6,386,418 B1 | * | 5/2002 | Garner ....................... 227/133 |
| 6,638,297 B1 | | 10/2003 | Huitema |
| 7,121,446 B2 | * | 10/2006 | Arad et al. ................ 227/176.1 |
| 2007/0106317 A1 | * | 5/2007 | Shelton et al. ............... 606/170 |

* cited by examiner

*Primary Examiner*—Rinaldi I. Rada
*Assistant Examiner*—Michelle Lopez
(74) *Attorney, Agent, or Firm*—Jacox, Meckstroth & Jenkins

(57) ABSTRACT

A sub-miniature surgical staple cartridge includes an elongated housing having longitudinally extending strips forming walls with a wall thickness preferably less than 0.015 inch. The walls define a plurality of longitudinally spaced pockets which receive a corresponding plurality of U-shaped surgical staples above generally flat corresponding drivers. The thin walls are formed of sheet metal or extruded plastics material or heat-formed sheet plastics material with the outer side walls having opposite end walls welded together or integrally connected. The outer side walls may be sheet metal enclosing sheet metal or plastic extruded internal walls, or the entire cartridge may be extruded of a plastics material or formed of sheet plastics material and have a plastic bottom wall.

15 Claims, 4 Drawing Sheets

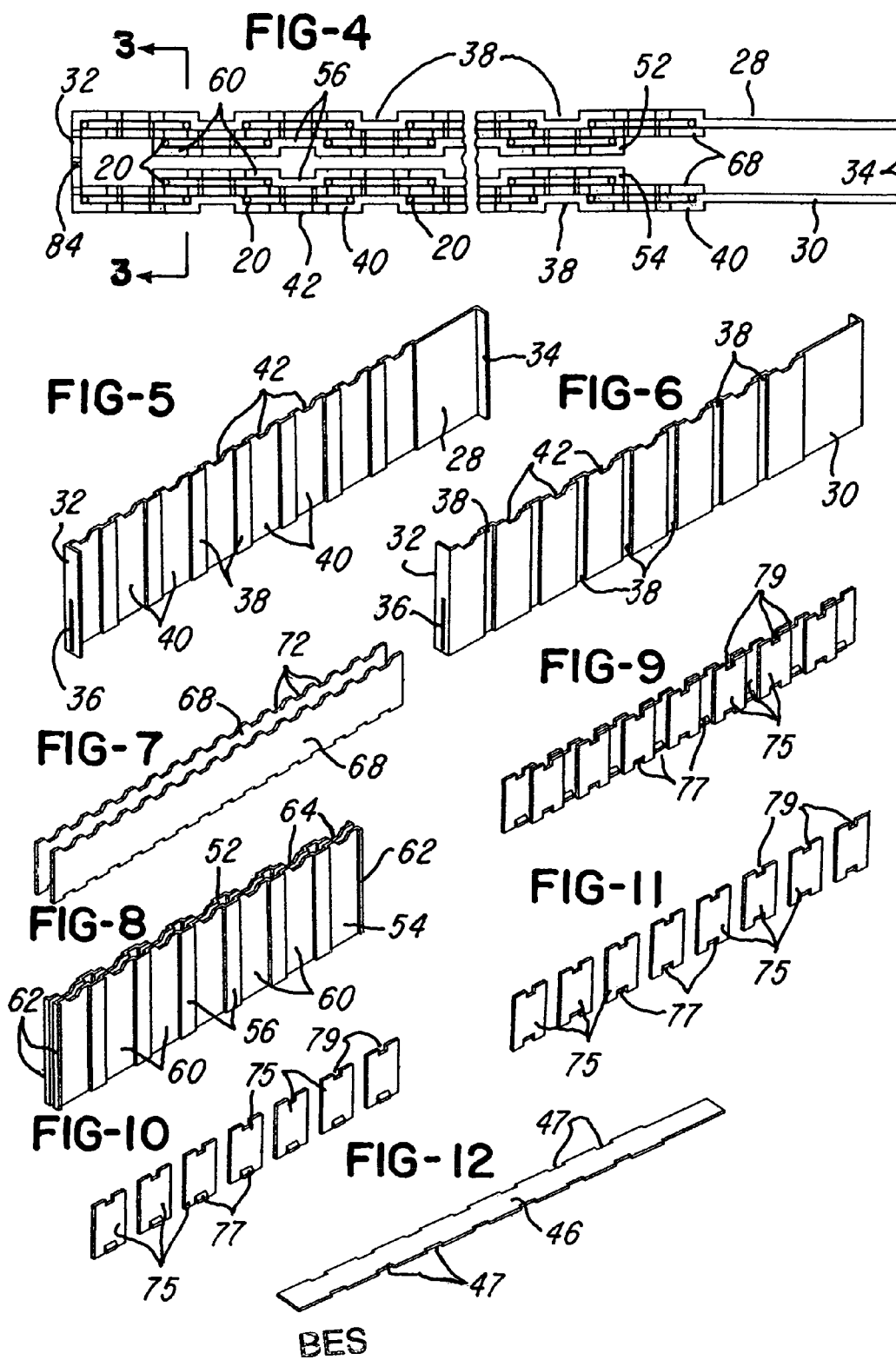

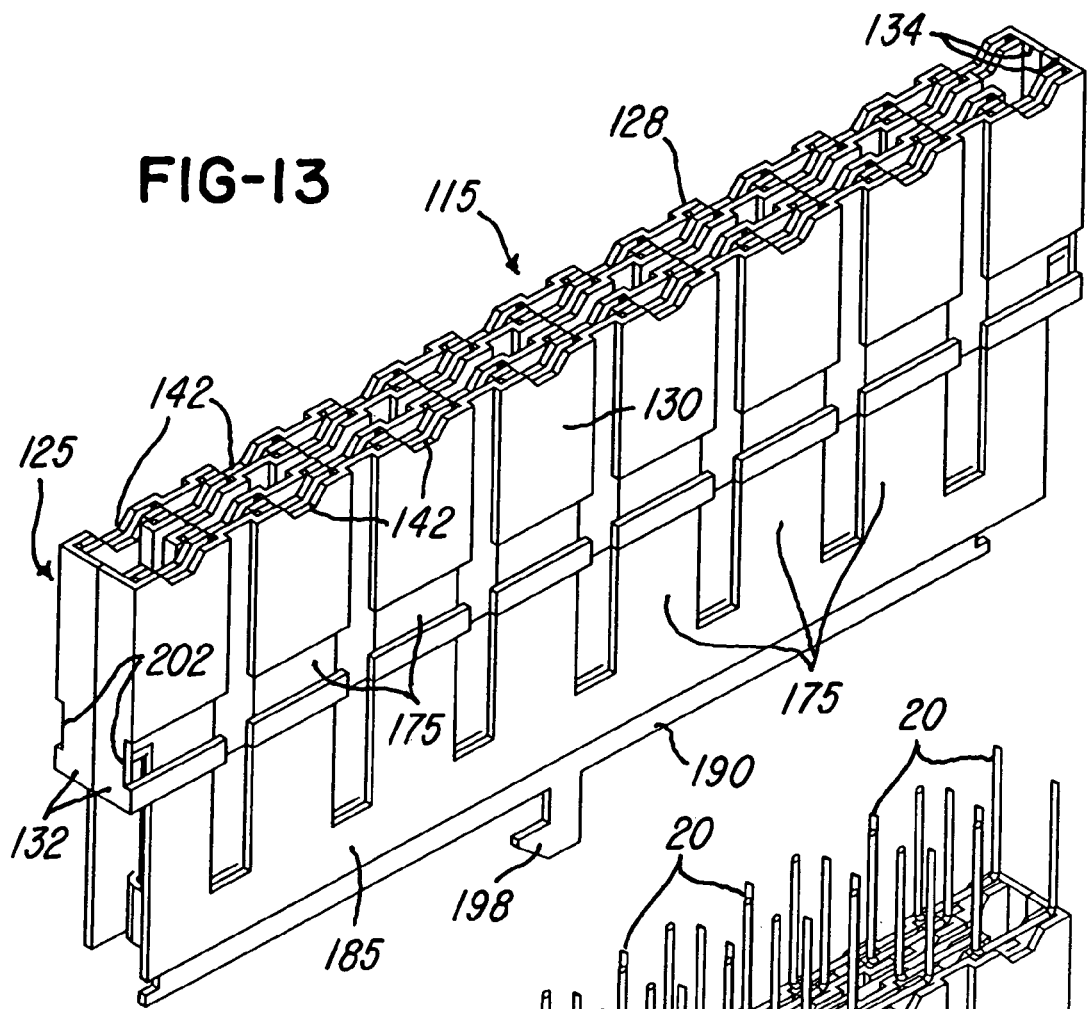
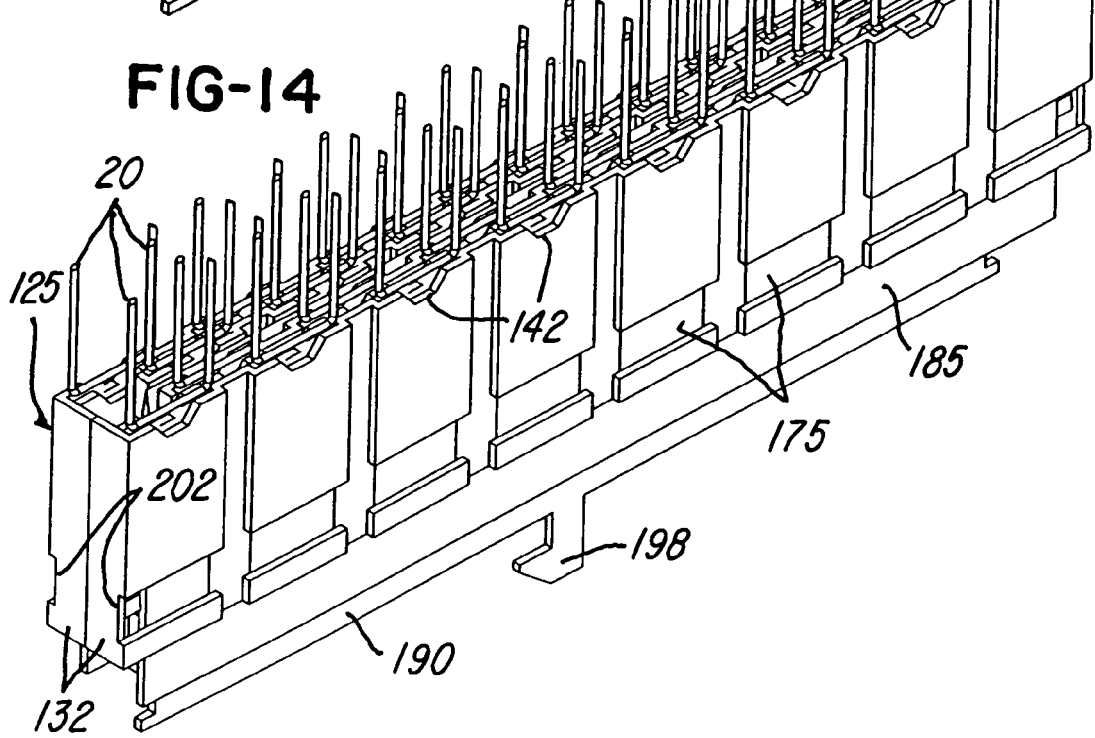

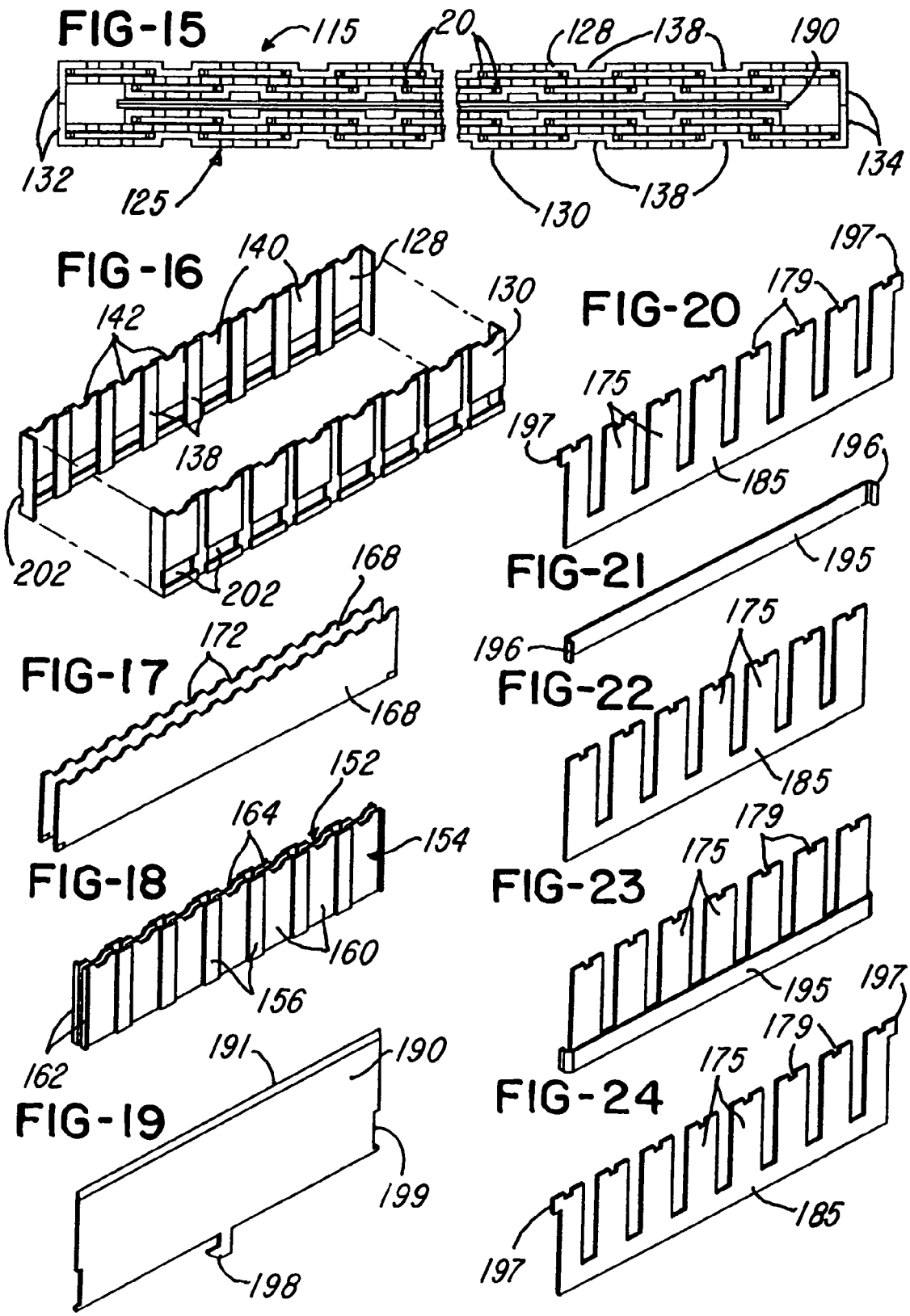

SUB-MINIATURE SURGICAL STAPLE CARTRIDGE

RELATED APPLICATION

This application claims the benefit of provisional application Ser. No. 60/763,571, filed Jan. 31, 2006.

BACKGROUND OF THE INVENTION

This invention relates to cartridges for surgical clips or staples and of the general type disclosed in U.S. Pat. No. 5,871,135 and U.S. Pat. No. 5,919,198, the disclosures of which are herein incorporated by reference. These patents disclose miniature cartridges for receiving multiple rows of very small surgical clips or staples, for example, of the B-Form or the type disclosed in U.S. Pat. No. 6,638,297. The staple cartridges are injection molded of a rigid plastics material and may be assembled in a manner similar to that shown in FIGS. 2-10 of the '198 patent, with each staple inserted into the cartridge having a corresponding molded plastic driver. The staple cartridge is loaded into an instrument or surgical stapler as disclosed in the '198 patent, and the staples are forced against an anvil carried by the stapler in response to actuation of staple drivers, for example, by a cam member which extends into the cartridge, as disclosed in the '135 patent. The cartridge may be provided with a slot between parallel rows of staples for receiving a longitudinally moveable knife blade for cutting the tissue or vessel located between the cartridge and the anvil after the tissue or vessel has been clamped by the staples.

SUMMARY OF THE INVENTION

It has been found desirable to provide for a sub-miniature surgical staple cartridge so that it may be used for stapling smaller and/or less accessible tissue and vessels and for using the cartridge within small vessels. Accordingly, the present invention is directed to a sub-miniature surgical staple cartridge which is substantially smaller and narrower in size than conventional staple cartridges, but provides for receiving the same commonly used staples. The staple cartridge of the invention may also be economically produced so that the cartridge may be disposable after it is used by the instrument or surgical stapler to insert the staples. The staple cartridge of the invention may be constructed to provide for a single row of staples or multiple rows of staples, for example, two rows, four rows or six rows. The cartridge may also provide for receiving a knife which moves between adjacent rows of staples for cutting the tissue or vessel between the two adjacent rows of staples after they have been progressively or simultaneously forced or driven into the anvil for deforming the staples to clamp the tissue or vessel.

In accordance with one illustrated embodiment of the invention, a sub-miniature elongated surgical staple cartridge is formed of thin wall material such as sheet metal or stainless steel sheet or extruded plastics material or sheet plastics material having a wall thickness, for example, less than 0.015 inch and on the order of 0.010 inch. The cartridge includes a housing formed by opposing and symmetrical outer shrouds or side walls each of which is stamped and formed or extruded or heat-formed to define parallel spaced cavities or pockets. The pockets receive a row of surgical staples, and the pockets also receive a corresponding row of stamped sheet metal or plastic drivers each having a laterally projecting tab. Inner walls may be spaced between the outer walls with each inner wall defining a series of longitudinally spaced cavities or pockets for also receiving corresponding rows of the drivers having laterally projecting tabs.

The surgical staples and drivers are retained within the pockets by thin parallel walls such as spaced elongated plates within an upper portion of the cartridge housing and by a sheet metal or plastic bottom wall or plate secured to the bottom edges of the outer side walls or integrally connecting the side walls. The upper edge surfaces of the parallel spaced outer side walls and inner walls are cut or trimmed to define longitudinally spaced recesses or undercuts which cooperate to define clearances for the staple tips when the staples are deformed into their desired clamped configuration. The outer side walls are connected by inwardly projecting end walls which define slots for receiving longitudinally moveable thin cam blades which progressively engage the tabs on the drivers for ejecting or firing the staples, and also define a slot for receiving a thin tissue cutting knife blade.

In another illustrated embodiment, the drivers are integrally connected in the general shape of a comb and move simultaneously within the pockets for simultaneously driving or firing the staples. The cutting knife blade is reciprocated in the same direction as the drivers and between adjacent rows of staples.

Other features and advantages of the invention will be apparent from the following description, the accompanying drawings and the appended claims.

BRIEF DESCRIPTION OF THE DRAWINGS

FIG. 4 is a top view of the cartridge shown in FIG. 1 with a center portion removed along with the actuating cam blades;

FIGS. 5-12 are perspective views of the thin wall components which are assembled to form the cartridge shown in FIGS. 1-4;

FIG. 13 is a perspective view of a greatly enlarged cartridge constructed in accordance with another embodiment of the invention and with multiple rows of surgical staples confined within the cartridge;

FIG. 14 is a perspective view of the cartridge shown in FIG. 13 and with the surgical staples pressed or ejected simultaneously from the cartridge;

FIG. 15 is a top view of the cartridge shown in FIG. 13 with a center portion broken away; and FIGS. 16-24 are perspective views, similar to FIGS. 5-12, of the thin wall components which are assembled to form the cartridge shown in FIGS. 13-14.

DESCRIPTION OF ILLUSTRATED EMBODIMENTS

Figure 1:
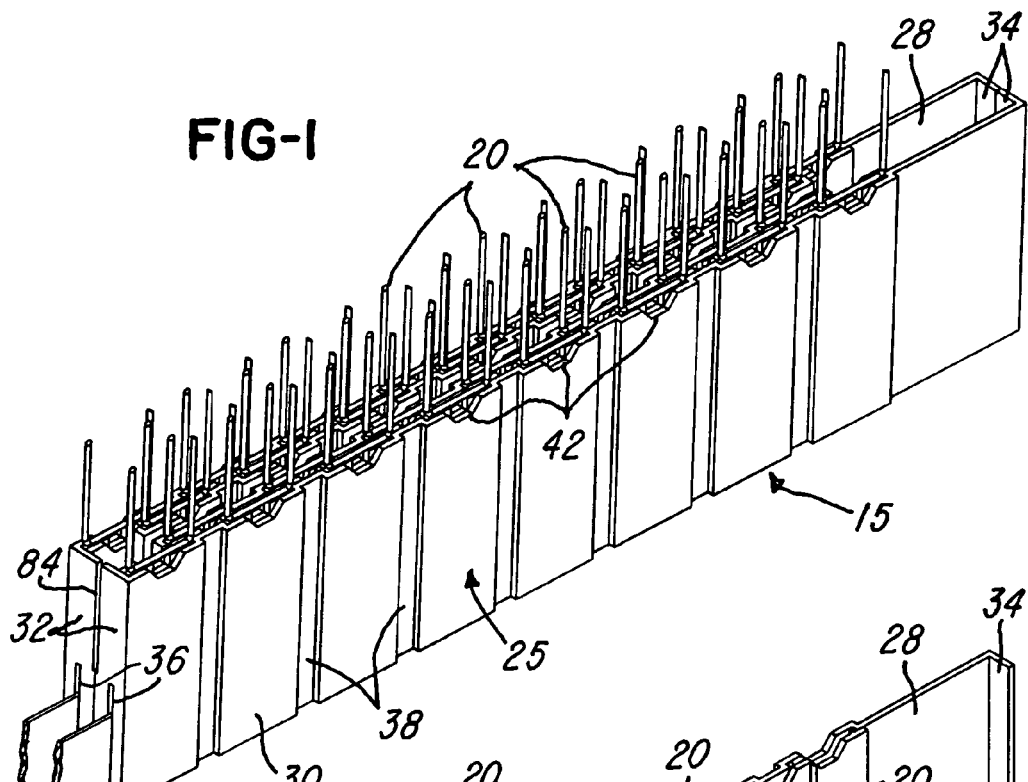
FIG. 1 is a perspective view of a greatly enlarged cartridge constructed in accordance with one embodiment of the invention and showing multiple rows of surgical staples in their ejected positions.

FIG. 1 illustrates, in greatly enlarged form, a sub-miniature surgical staple cartridge 15 constructed in accordance with the invention and of which all components are formed of material having thin walls such as thin stainless steel sheet or thermoplastic sheet or an extrusion of plastics material, such as polycarbonate and forming walls of substantially uniform thickness of less than 0.015 inch and about 0.010 inch plus or minus 0.003 inch. The cartridge 15 is shown to hold four rows of surgical clips or staples 20 each having generally a U-shaped configuration. However, the cartridge 15 may be constructed to hold more or less rows of staples, for example, one row, two rows or six rows. Each of the parallel rows is shown in FIG. 1 with eight staples. However, each row may have more or less staples, depending upon the use of the cartridge. As shown, the cartridge 15 may have an overall width less than 0.150 inch as compared to a molded plastic cartridge having a width over 0.400 inch.

The cartridge 15 includes an elongated housing 25 formed by a pair of opposing and symmetric outer shrouds or side walls 28 and 30 (FIGS. 5 and 6) each of which may be formed from a thin sheet of plastics material or a thin sheet of stainless steel or as an extrusion. Each of the side walls 28 and 30 has parallel end walls 32 and 34 which project at right angles, and each end wall 32 has a lower portion with a slot 36. Each of the side walls 28 and 30 is formed with parallel spaced ribs 38 defining therebetween rectangular cavities or pockets 40, and the top edge surface of each side wall is notched to form a recess or undercut 42 for each pocket 40. When the side walls 28 and 30 are assembled, as shown in FIGS. 1 & 4, the abutting end walls 32 and 34 are secured together, for example, by laser welding or soldering. However, it is within the scope of the invention to form both side walls 28 and 30 as a one-piece plastic extrusion or from one single strip of sheet metal or sheet plastic whereby the opposing end walls 32 and/or the opposing end walls 34 are integrally connected.

The cartridge 15 also includes an elongated flat bottom wall 46 (FIG. 12) in the form of a die-cut strip of sheet plastic or a strip of thin sheet metal, and opposite edge surfaces of the bottom wall 46 have longitudinally spaced notches 47 which receive the inwardly projecting ribs 38 defining the pockets 40 in the opposite side walls 28 and 30. The bottom wall 46 is rigidly secured or connected to the side walls 28 and 30, for example, by adhesive or laser welding, and opposite ends of the bottom wall 46 are similarly connected or welded to the end walls 32 and 34 of the side walls 28 and 30. Sheet metal or plastic side walls 28 and 30 may also be integrally connected by a bottom wall 46 and formed from a single strip of material.

A pair of parallel spaced elongated internal walls 52 and 54 (FIG. 8) are positioned within a center portion of the cartridge 15, and each internal wall is formed as an extrusion or from a sheet of plastics material or as a sheet metal stamping and includes parallel ribs 56 defining therebetween parallel spaced cavities or pockets 60. Each of the internal walls 52 and 54 have opposite end tabs 62 which project laterally outwardly at right angles and serve to position the internal walls 52 and 54 within the cartridge 15. Longitudinally spaced recesses or undercuts 64 are formed within the top or outer edge of each internal wall 52 and 54 in the same configuration as the undercuts 42 are formed within the edge portions outer side walls 28 and 30.

A pair of flat plastic or sheet metal separator walls or plates 68 (FIG. 7) are positioned on opposite sides of the internal walls 52 and 54. The plates 68 contact the upper portions of the ribs 38 on the outer side walls 28 and 30 and also contact the ribs 56 on the internal walls 52 and 54. The flat walls or plates 68 serve to close the upper portions of the parallel spaced pockets 40 and 60 to retain the staples, and longitudinally spaced recesses or undercuts 72 are formed within the upper edges of the plates 68 and align with the undercuts 42 and 64 within the outer side walls 28 and 30 and the internal walls 52 and 54.

Referring to FIGS. 9-11, individual drivers 75 are confined within the pockets 40 and 60 for lateral or vertical sliding movement, and each driver 75 is formed from a plastics sheet material or from thin sheet metal or stainless steel with a laterally projecting tab 77 in its bottom portion and a notch 79 in its top edge surface. The drivers 75 are confined within the lower portions of the pockets 40 and 60, and a metal surgical staple 20 is confined within the upper portion of each pocket directly above the corresponding driver 75. FIG. 9 illustrates how the drivers 75 are longitudinally staggered within the pockets 40 of each side wall and the pockets 60 within the opposing internal wall 52 or 54. Adjacent drivers 75 are laterally spaced by the thickness of the corresponding flat separator plate 68, as shown in FIGS. 2 & 3.

Figure 2:
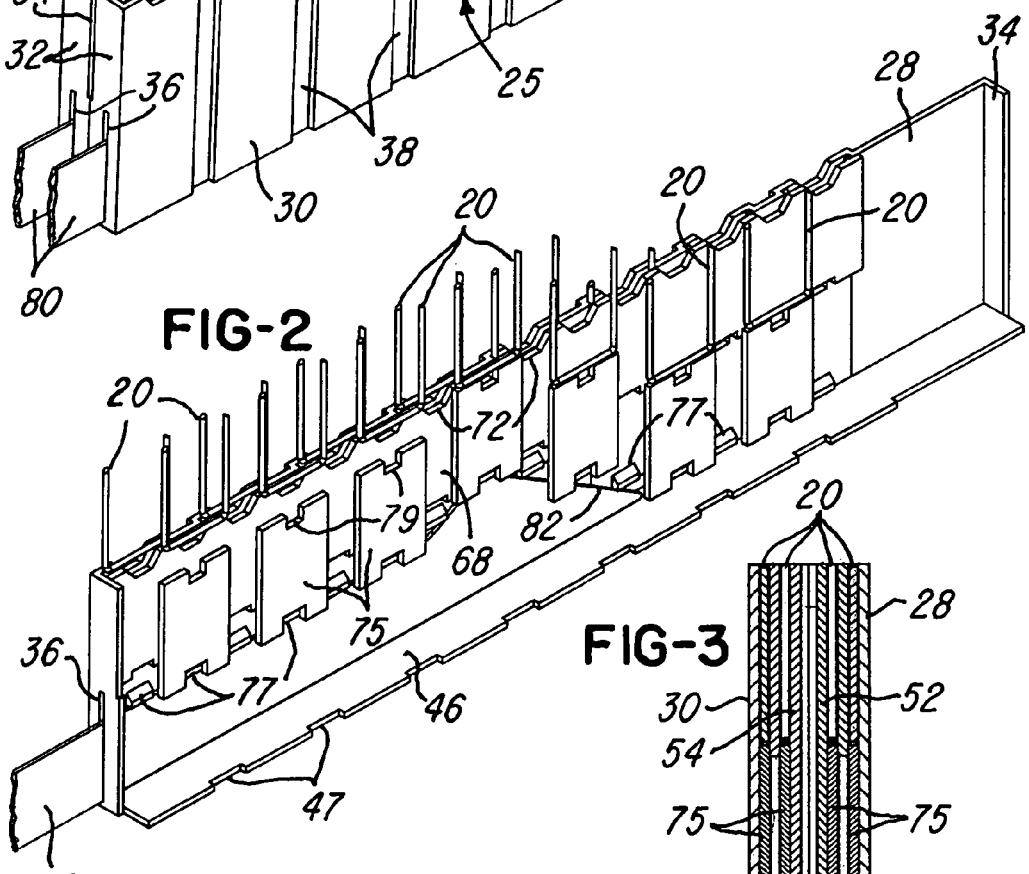
FIG. 2 is a fragmentary perspective view of one side portion of the cartridge of FIG. 1 and showing the driver plates being shifted to eject the staples in response to the longitudinal movement of an actuating cam blade.
Figure 3:
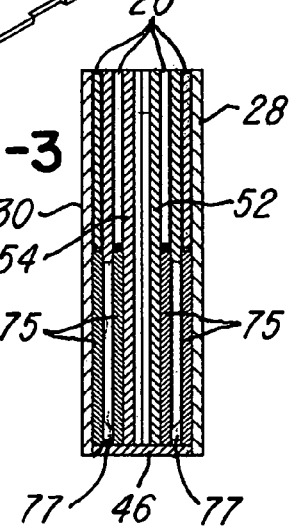
FIG. 3 is an enlarged (over 6 times) vertical cross-section of the cartridge shown in FIG. 1 and taken generally on the line 3-3 of FIG. 4.

Referring to FIG. 2, after the cartridge 15 is loaded with staples 20 and the drivers 75 in their retracted positions within the pockets 40 and 60, as shown at the right in FIG. 2, the loaded cartridge is inserted into an instrument or stapler (not shown), for example, of the general type disclosed in the above '135 Patent. When the stapler is actuated, a pair of parallel spaced cam blades 80 (FIGS. 1 & 2) are extended longitudinally into the cartridge 15 through the slots 36. Each of the blades 80 has an inclined forward end cam surface 82 which progressively engages the tabs 77 on two adjacent rows of driver plates 75 and forces the drivers and the corresponding staples 20 upwardly or outwardly within the corresponding pockets 40 and 60. The legs of the staples 20 pierce the tissue or vessel and engage the anvil within the stapler, and the anvil folds the legs of the staples inwardly, in a conventional manner, to clamp the vessel or tissue with the four parallel spaced rows of staples. The instrument or stapler then extends an elongated cutting knife (not shown) through a slot 84 (FIG. 1) defined between the upper portions of the end walls 32 of the cartridge 15 and between the spaced internal walls 52 and 54, and the knife cuts the vessel or tissue between the inner two rows of staples, in a conventional manner.

Referring to FIGS. 13-15 which illustrate another embodiment of the invention, a sub-miniature surgical staple cartridge 115 is constructed in a manner similar to the staple cartridge 15 described above in connection with FIGS. 1-12, and all of the components of the cartridge 115 are formed from thin sheets of plastics material or from thin sheet metal or as from extrusions having walls with a thickness of less that 0.015 inch and about 0.010 inch plus or minus 0.003 inch. Accordingly, the same reference numbers are used in FIGS. 13-24 for components corresponding to the similar components in FIGS. 1-12, except with the addition of "100" in FIGS. 13-24. Also, while the cartridge 115 is shown with four rows of surgical clips or staples 20, the cartridge may be constructed to hold more or less rows of staples with each row having more or less than the eight staples as shown in each row.

The primary difference between the cartridge 115 and the cartridge 15 is that the drivers 175 are integrally connected by a longitudinally extending edge portion 185 so that the drivers 175 move simultaneously within the pockets 140 and 160. Thus the drivers 175 press each row of surgical staples 20 simultaneously through the tissue and into the elongated anvil within the surgical instrument for deforming the staples into their clamping positions. Similarly, an elongated metal cutting knife 190 (FIG. 19) has a razor sharp edge 191 and moves between the internal walls 152 and 154, as shown in FIG. 15, to cut the vessel or tissue between the inner two rows of staples after the vessel or tissue has been clamped by the staples.

As shown in FIGS. 21 and 23, the staple cartridge 115 also includes a pair of elongated sheet metal or plastic spacer strips 195 which have opposing and connected end tabs 196 for retaining the strips of drivers 175 within the pockets 160. The strips of drivers 175 shown in FIGS. 20 and 24 also have end tabs 197 for retaining the strips of drivers within the cartridge 115. The cutting knife 190 also has an integrally projecting hook portion 198 which is used for retracting the knife 190 back into the cartridge 115 between the internal pocket defining walls 152 and 154 after the knife has cut the tissue. Opposite end portions of the knife 190 also include notches or recesses 199 which function to retain the knife 190 within the cartridge 115, and each of the outer shrouds or side walls 128 and 130 (FIG. 16) is provided with a longitudinally extending grooves 202 for locating the cartridge 115 within the surgical instrument. The grooves 202 may be in the lower portions of the side walls of the cartridge 15 or 115 (FIG. 4) or in the upper portions of the side walls.

From the drawings and the above description, it is apparent that a surgical staple cartridge constructed in accordance with the invention provides for substantially reducing the size or width of a staple cartridge and thus permits the cartridge to be used with smaller or miniaturized surgical devices and in more confined and restricted spaces for surgical procedures within a person's body. The construction of the cartridges 15 and 115 also provides the sub-miniature cartridge with substantial rigidity. If the cartridge 15 or 115 is formed of stainless sheet metal, the cartridge may be reused by sanitizing the cartridge within an autoclave. The configuration of the undercuts 42, 64 and 72 and the notches 79 in the embodiment of FIGS. 1-12 and the corresponding undercuts and notches within the embodiment of FIGS. 13-24 cooperate with the anvil to close and clamp the staples in a desired manner.

While the form of staple cartridges and their methods of construction herein described constitute preferred embodiments of the invention, it is to be understood that the invention is not limited to these precise forms of cartridge, and that changes may be made therein without departing from the scope and spirit of the invention as will be defined later in the claims. For example, while the side walls 28 and 30 and 128 and 130 are shown and described above as separate pieces, the side walls may be integrally connected by one end wall or a bottom wall if the cartridge is formed from a single strip of sheet metal or plastics material with the side walls folded from the end wall or bottom wall after the pockets and undercuts are formed. The side walls may also be integrally connected by both end walls if the side walls are formed as a one-piece extrusion of plastics material. It is also within the scope of the invention for the parallel spaced inner walls 52 and 54 shown in FIG. 8 or inner walls 152 and 154 shown in FIG. 18 to be made from a single strip of sheet material or as an extrusion and be integrally connected by a bottom wall or end walls. It is also within the scope of invention to form all the walls or all of the internal walls of cartridge 15 or 115 from a one-piece extrusion of plastics material and then attach a bottom wall by an adhesive or laser welding.

What is claimed is:

1. A surgical staple cartridge supporting a plurality of parallel rows of miniature generally U-shaped surgical staples, said cartridge comprising
    an elongated sheet metal housing comprising longitudinally extending elongated sheet metal strips each having a substantially uniform thickness less than 0.015 inch,
    at least two of said sheet metal strips forming parallel spaced sheet metal side walls for said housing with opposite end portions of said side walls connected together to define a space between said side walls,
    each of said sheet metal strips forming said side walls having a plurality of longitudinally spaced U-shaped integral sheet metal ribs of uniform wall thickness and extending laterally across said strip to define a row of longitudinally spaced pockets between said ribs,
    at least one of said elongated sheet metal strips being substantially flat and extending longitudinally within said space between said sheet metal side walls and closing said pockets,
    a plurality of said elongated sheet metal strips forming longitudinally extending internal walls positioned within said space between said sheet metal side walls,
    each of said internal walls forming a plurality of longitudinally spaced U-shaped integral sheet metal ribs defining a row of said pockets between said ribs,
    one of said surgical staples supported within each of said pockets in said side walls and said internal walls for lateral sliding movement, and
    a plurality of substantially flat drivers within said pockets and supported for lateral sliding movement within said pockets to eject said staples from said pockets.

2. A cartridge as defined in claim 1 wherein each of said sheet metal strips forming said side walls has a longitudinally extending top edge portion defining longitudinally spaced recesses in lateral alignment with said pockets.

3. A cartridge as defined in claim 1 wherein each of said sheet metal strips has a substantially uniform thickness of about 0.010 inch.

4. A cartridge as defined in claim 1 wherein each of said flat drivers comprise sheet metal of uniform thickness and having a laterally projecting integral sheet metal tab adapted to be engaged by a cam member sliding longitudinally adjacent said drivers.

5. A cartridge as defined in claim 1 wherein said opposite end portions of said sheet metal strips forming said side walls comprise laterally projecting and opposing end walls rigidly connected to define said space between said side walls.

6. A cartridge as defined in claim 1 wherein said end portions of said sheet metal side walls are rigidly connected by welds.

7. A surgical staple cartridge supporting a row of miniature generally U-shaped surgical staples, said cartridge comprising
    an elongated sheet metal housing comprising a set of separate longitudinally extending elongated sheet metal strips each having a substantially uniform wall thickness less than 0.015 inch and extending the entire length of said housing,
    one of said sheet metal strips forming a longitudinally extending sheet metal side wall for said housing,
    said sheet metal strip forming said side wall being deformed to define a plurality of longitudinally spaced U-shaped integral sheet metal ribs each having said uniform wall thickness and extending laterally across said strip to define a row of longitudinally spaced and longitudinally extending elongated pockets between said ribs,
    one of said elongated sheet metal strips being substantially flat and extending longitudinally adjacent said ribs of said sheet metal side wall and closing said pockets,
    one of said surgical staples supported within each of said pockets for lateral sliding movement,
    a plurality of substantially flat drivers within said pockets and supported for lateral sliding movement within said pockets to eject said staples from said pockets, and
    said sheet metal strip forming said side wall has a longitudinally extending top edge portion defining longitudinally spaced recesses in lateral alignment with said pockets.

8. A cartridge as defined in claim 7 wherein each of said sheet metal strips has a substantially uniform thickness of about 0.010 inch.

9. A cartridge as defined in claim 7 wherein said sheet metal strip forming said side wall has right angle projecting and parallel opposite end walls.

10. A surgical staple cartridge supporting a plurality of rows of miniature generally U-shaped surgical staples, said cartridge comprising an elongated sheet metal housing comprising longitudinally extending elongated sheet metal strips each having a substantially uniform wall thickness less than 0.015 inch, two of said sheet metal strips forming longitudinally extending sheet metal side walls for said housing, said sheet metal strips forming said side walls each having a plurality of longitudinally spaced U-shaped integral sheet metal ribs each having said uniform wall thickness and extending laterally across said strip to define a row of longitudinally spaced and longitudinally extending elongated pockets between said ribs, one of said elongated sheet metal strips being substantially flat and extending longitudinally adjacent said ribs of one of said sheet metal side walls and closing said pockets, one of said surgical staples supported within each of said pockets for lateral sliding movement, and a plurality of substantially flat drivers within said pockets and supported for lateral sliding movement within said pockets to eject said staples from said pockets.

11. A cartridge as defined in claim 10 wherein each of said sheet metal strips forming said side walls has a longitudinally extending top edge portion defining longitudinally spaced recesses in lateral alignment with said pockets.

12. A cartridge as defined in claim 10 wherein each of said sheet metal strips has a substantially uniform thickness of about 0.010 inch.

13. A cartridge as defined in claim 10 wherein each of said flat drivers comprise sheet metal of uniform thickness and having a laterally projecting integral sheet metal tab adapted to be engaged by a cam member sliding longitudinally adjacent said drivers.

14. A cartridge as defined in claim 10 wherein each of said sheet metal strips forming said side walls has right angle projecting and parallel opposite end walls.

15. A cartridge as defined in claim 14 wherein corresponding said end walls of said sheet metal side walls are opposing and rigidly connected by welds.

\* \* \* \* \*